United States Patent [19]

Krone et al.

[11] Patent Number: 5,700,459
[45] Date of Patent: Dec. 23, 1997

[54] PHARMACOLOGICAL COMPOSITION CONTAINING POLYELECTROLYTE COMPLEXES IN MICROPARTICULATE FORM AND AT LEAST ONE ACTIVE AGENT

[75] Inventors: Volker Krone, Flörsheim am Main; Michael Magerstädt, Hofheim am Taunus; Axel Walch, Frankfurt am Main; Albrecht Gröner, Seeheim-Jugenheim; Dieter Hoffmann, Marburg, all of Germany

[73] Assignee: Hoechst Aktiengesellschaft, Frankfurt am Main, Germany

[21] Appl. No.: 341,164

[22] Filed: Nov. 16, 1994

Related U.S. Application Data

[63] Continuation of Ser. No. 88,581, Jul. 9, 1993, abandoned, which is a continuation of Ser. No. 689,643, Apr. 23, 1991, abandoned.

[30] Foreign Application Priority Data

| Apr. 25, 1990 | [DE] | Germany | 40 13 110.6 |
| Nov. 6, 1990 | [DE] | Germany | 40 35 187.4 |

[51] Int. Cl.$^6$ ..................................... A61K 9/14
[52] U.S. Cl. .................. 424/78.08; 424/94.1; 424/184.1; 424/489; 424/499; 424/500; 424/501; 514/2; 514/951; 128/660.01
[58] Field of Search .................... 424/78.08, 484, 424/489, 499, 500, 501, 184.1, 94.1; 514/2, 951; 128/660.01

[56] References Cited

U.S. PATENT DOCUMENTS

| 4,409,331 | 10/1983 | Lim | 435/178 |
| 4,487,758 | 12/1984 | Goosen et al. | 424/21 |
| 4,495,288 | 1/1985 | Jarvis, Jr. et al. | 435/241 |
| 4,663,286 | 5/1987 | Tsang et al. | 435/178 |
| 4,741,872 | 5/1988 | De Luca | 424/501 |
| 4,835,248 | 5/1989 | Bader et al. | 528/328 |
| 4,940,588 | 7/1990 | Sparks | 424/489 |

FOREIGN PATENT DOCUMENTS

| 2012311 | 9/1990 | Canada . |
| 0127989A3 | 12/1984 | European Pat. Off. . |
| 0127713A3 | 12/1984 | European Pat. Off. . |
| 0152898 | 8/1985 | European Pat. Off. . |
| 0152898A2 | 8/1985 | European Pat. Off. . |
| 0188309A2 | 7/1986 | European Pat. Off. . |
| 0 388 758 | 9/1990 | European Pat. Off. . |
| 0 392 487 | 10/1990 | European Pat. Off. . |
| 1 183 403 | 3/1970 | United Kingdom . |
| 2 153 780 | 8/1985 | United Kingdom . |

OTHER PUBLICATIONS

Michaels, A. S., "Polyelectrolyte Complexes," J. Indust. & Eng. Chem., 57(10): 32–40 (1965).

Petrak, K., "Polyelectrolyte Complexes in Biomedical Applications," J. Bioactive & Compatible Biopolymers, 1: 202–219 (1986).

A. Johansen, et al., "Immobilization of Yeast Cells by Internal Gelation of Alignate," Enzyme Microb. Technol. vol. 8, (1987).

C. A. Finch, "Polymers for Microcapsule Walls," Chemistry and Industry, pp. 752–756, (1985).

Encyclopedia of Chemical Technology, "Microencapsulation," pp. 1A–25A, vol. 15, Third Edition, (1981).

C.E. Camp, et al., "Calcium Alginate–Immobilized Hepatic Microsomes: Effect of NADPH Factor on Oxidation Rates," pp. 685–689 Enzyme Micro. Technol., vol. 9, (1987).

*Primary Examiner*—Raj Bawa
*Attorney, Agent, or Firm*—Finnegan, Henderson, Farabow, Garrett & Dunner, L.L.P.

[57] ABSTRACT

The invention relates to a pharmacological composition comprising a polyelectrolyte complex, in particular a polyacid with an average particle size of less than 15 μm and an active agent, among which are active peptides, proteins, enzymes, enzyme inhibitors, antigens, cytostatics, antiinflamatory agents, antibiotics and vaccines. The said composition ensures that the active agent is converted in a nondeleterious manner into a form which can be administered. In addition, the biodistribution, bioavailability and absorption of the pharmaceutical are beneficially affected.

13 Claims, No Drawings

PHARMACOLOGICAL COMPOSITION CONTAINING POLYELECTROLYTE COMPLEXES IN MICROPARTICULATE FORM AND AT LEAST ONE ACTIVE AGENT

CROSS-REFERENCE TO RELATED APPLICATIONS

This application is a continuation of application Ser. No. 08/088,581, filed Jul. 9, 1993, abandoned, which is a continuation of application Ser. No. 07/689,643, filed Apr. 23, 1991, abandoned.

BACKGROUND OF THE INVENTION

1. Field of the Invention

The invention relates to pharmacological compositions which contain polyelectrolyte complexes in microparticulate form and at least one active substance. The active substance can in this case be embedded in the matrix of the polyelectrolyte complex, itself be a partner in the polyelectrolyte complex or be bound to a partner of the polyelectrolyte complex. By active substances are meant primarily pharmacological active substances such as active peptides, proteins, enzymes, enzyme inhibitors, antigens, cytostatics, antibiotics, antiinflammatory agents or vaccines. In the particular case of ultrasonic diagnostic aids, also meant as active substances in this connection are contrast agents such as gases, for example air, oxygen or inert gases.

2. Description of the Prior Art

It is known from the literature that multiple charged macromolecular compounds with ions of opposite charge form ionic compounds which may, depending on the charge distribution and the molecular weight of the final product, precipitate from aqueous solutions. In this case, low molecular weight ions of the same charge are displaced by the higher molecular weight compound. These phenomena are also collected together under the overall term "polyelectrolyte effect". State of the art are, inter alia, the formation of gels by mixing alginate solutions and $Ca^{2+}$. Protein precipitations also take place in some cases in accordance with this principle. Polyelectrolyte complexes can in principle be composed of a macromolecular, multiply charged component of one polarity and many low molecular weight ions of the other polarity, or else of two macromolecular partners, each of which is multiply charged with different polarity. Hollow capsules which are prepared from such polyelectrolyte complexes are described, for example, in BE-A 901.704, EP-A 0 127 989, EP-A 0 188 309, EP-A 0 127 713, DE-A 32 09 127, EP-A 0 152 898, U.S. Pat. No. 4,487,758, DE-A 32 09 098, U.S. Pat. No. 4,409,331, A. Johansen and J. M. Flink, Enzyme Mikrob. Technol., 1986, vol. 8, 145–148 or C. E. Camp and S. S. Sofer, Enzyme Mikrob. Technol., 1987, vol. 9, 685–689.

Formulations and active substance combinations which not only convert the active substance in a non-deleterious manner into a form which can be administered but also have a specific effect on the biodistribution, bioavailability or absorption of the pharmaceutical are becoming increasingly important in modern pharmaceutical technology. It is possible therewith to achieve both new therapeutic and diagnostic areas of use and, for example, an increase in the therapeutic index of an active substance. Particulate systems of extremely small diameter (so-called micro- or nanoparticles) in particular have suggested themselves recently as important administration form, both in the oral and in the parenteral area. Usually employed in this connection as carrier substances are biocompatible, biodegradable polymers.

SUMMARY OF THE INVENTION

It has now been found, surprisingly, that polyelectrolyte complexes show to a particular extent properties, both as carrier substances and as active substance components, which meet the profile of requirements of biocompatible (biodegradable) polymer systems and can be adapted to meet the various requirements. It was known of hollow capsules, including polyelectrolyte complex capsules, that active substance incorporation capacities of 90% and more can be achieved. This was not to be expected with microparticles which are composed of just such polyelectrolyte complexes, because these complexes form only at the interface (around the active substance). This particularly applies when they are prepared from purely aqueous reaction solutions into which active substances, which are soluble therein, are introduced. It was therefore all the more surprising that particulate polyelectrolyte complexes also display incorporation capacities of more than 90%. It was furthermore surprising that in the preparation of such polyelectrolyte complex matrices there was formation of fine particles in the µm range or emulsions and not, as was really to be expected, an agglomerated mass. It is possible according to the invention to prepare such colloidal systems of micro/nanoparticles especially well from polyelectrolyte complexes. There is then in vivo, via solution equilibria and charge interactions, a slow decomplexation as well as a breakdown of complexands, which results in dissolution of the complex and release of the active substance. These release conditions can, as can the consistency properties, be controlled via the composition of the complex.

DESCRIPTION OF THE PREFERRED EMBODIMENTS

The partners employed for the complex formation are preferably biocompatible, biodegradable polyacids and polybases which are naturally occurring or composed of natural subunits. In this case, "poly" means that the compound carries more than one charge of the same polarity, preferably a large number of such charges. The particular counterions can be composed either of low molecular weight ions or likewise of a polyionic species. Either one or both ionic partners can be either inorganic or organic in nature. In the case of organic polyions, hydrophobic substituted derivatives prove suitable and preferable.

Preferred materials for the preparation of biocompatible polyelectrolyte complex/active substance combinations are, as polyacids: xylan polysulfate, partially hydrophobically esterified xylan polysulfate, polysulfates of other polysaccharides such as, for example, starch hydrolysates, inulin, hydroxyethylstarch, dextrans and the partially hydrophobically substituted derivatives thereof in each case, and poly (amino acids) such as polyaspartic acid or polyglutamic acid and the hydrophobically substituted derivatives thereof in each case. As polybases: poly-L-lysine of various defined molecular weight ranges, poly-α,β-(2-dimethylaminoethyl)-D,L-aspartamide (PDAA), copolymers of PDAA and hydrophobically esterified poly-α,β-(2-hydroxyethyl)-D,L-aspartamide (PHEA), chitosan, lysine octadecyl ester, aminated dextrans, aminated cyolodextrins, aminated cellulose ethers, aminated pectins and the partially hydrophobically substituted derivatives thereof in each case.

In one preferred embodiment, the polyelectrolyte complex contains a polyacid which is selected from: xylan polysulfates, dextran sulfates, poly(amino acids) such as polyaspartic acid or polyglutamic acid, polysaccharide polysulfates such as sulfates of starch hydrolysates, inulin, hydroxyethylstarches, polysaccharide polysulfonates, polysaccharide polyphosphates, polyphosphates, and, more preferably, the polyelectrolyte complex contains a polyacid which is selected from: in each case partially hydrophobized (for example etherified, esterified) derivatives of xylan polysulfate, polysulfates of other polysaccharides such as, for example, starch hydrolysates, inulin, hydroxyethylstarches, dextrans; of poly(amino acids) such as polyaspartic acid or polyglutamic acid, and of polysaccharide polysulfonates, polysaccharide polyphosphonates, polyphosphates.

In another preferred embodiment, the polyelectrolyte complex contains a polybase which is selected from: poly-L-lysine, poly-α,β-(2-dimethylaminoethyl)-D,L-aspartamide, chitosan, lysine octadecyl ester, aminated dextrans, aminated cyclodextrine, aminated cellulose ethers, aminated pectins, and, more preferably, the polyelectrolyte complex contains a polybase which is selected from: in each case (for example by partial or complete esterification and/or etherification) hydrophobized derivates of: poly-L-lysine of various molecular weight ranges, poly-α,β-(2-dimethylaminoethyl)-D,L-aspartamide, chitosan, aminated dextrans, aminated cyclodextrins, aminated cellulose ethers, aminated pectins and copolymers of poly-α,β-(2-dimethylaminoethyl)-D,L-aspartamide and hydrophobically esterified poly-α,β-(2-hydroxyethyl)-D,L-aspartamide.

Microparticles composed of polyelectrolyte complexes can, depending on the requirements, be prepared in average particle sizes from a few nm up to a few hundred μm. It is also possible by definition for the microparticles to be in the form of emulsions. The breadth of the size distribution can be adjusted, for example by the stirring speed on mixing the polyelectrolytes, the drop rate, the nozzle diameter, the pH and by suitable choice of the polyelectrolyte partners. It is particularly advantageous to carry out the formation of the complexes with addition of auxiliaries such as amphiphilic molecules (for example ® Pluronic) or colloidal substances (for example adjuvants) with high incorporation capacity. These parameters can be determined in simple routine tests and adjusted to the required particle size and particle size distribution. Particles below 5 μm in diameter are suitable for intravenous injection. Particles with a diameter <15 μm, preferably <10 μm can be employed as s.c. or i.m. injectable depot forms and as a vehicle to increase the enteral absorption.

The incorporation of an active substance in the polyelectrolyte complex particles/colloids can be carried out in at least 4 ways: a) incorporation by "entrapment" of the active substance, which is present in solution, on precipitation of the complex, b) incorporation by absorption of the active substance from a solution with which the already prepared polyelectrolyte complexes come into contact (especially in the case of porous materials or gels with "sponge" properties), c) precipitation of the polyelectrolyte complex, in which case the active substance is chemically bound to at least one complex partner and, d) incorporation by employing the active substance as partner in the formation of the polyelectrolyte complex. This usually requires at least one charge or polarizable group on the active substance. The invention therefore also relates to a process for preparing pharmaceutical compositions containing polyelectrolyte complexes and active substances, where a solution of an acidic and a solution of a basic substance, where at least one of these substances must be polymeric, are mixed and where a) either one of the partners is an active substance or contains the latter in chemically bound form, or b) the active substance is contained in one of the solutions, and subsequently the resulting polyelectrolyte complex is precipitated in microparticulate form or, where appropriate, converted into a microparticulate form.

Polyelectrolyte complex/active substance formulations show, because the consistency properties can be widely varied on the one hand and can be very specifically adjusted on the other hand, property profiles as required for diverse pharmaceutical applications.

Thus, it has emerged that the cytostatic daunorubicin and the polyacid xylan polysulfate produce macroparticles which contain daunorubicin and release the latter in buffer solution or in biological systems uniformly over a lengthy period, during which they are broken down. If polybases are also added and/or the polyacid is changed, especially by replacing xylan polysulfate by xylan polysulfate which is partially substituted with palmitoyl ester groups, it is possible to reduce the particle size to <<5 μm and the result is an i.v. injectable system with the release properties described above. The therapeutic index of the cytostatic can be drastically increased with a slow-release form of this type. The activity properties of other low molecular weight active substances such as antibiotics (for example tetracycline) or other cytostatics can also be distinctly improved in this way.

If proteins are incorporated in polyelectrolyte complex microparticles, it is possible in this way both to protect them from hydrolytic attack and to achieve controlled release profiles. Thus, for example, vaccine preparations can be produced using vital proteins or similar substances suitable for vaccination and can, depending on the particle size, be injected i.m. or even administered orally, in which case there is absorption in the gastrointestinal tract of particles <5 μm, and subsequent antigen expression/immunization occurs. It is possible, with such antigen-containing polyelectrolyte complexes according to the invention, to achieve release profiles which allow a large dose of the vaccine to be delivered shortly after administration and after a period of, for example, 4 weeks (booster). The substances particularly suitable for forming polyelectrolyte complexes in this case are described in Example 3.

It is also possible to convert peptide-based active substances by means of polyelectrolyte complex preparations into suitable long-term systems. These formulations are in some cases superior to the known polymeric depot systems for LHRH analogs, for example, both because the degradability is better and because the release profiles are defined.

Polyelectrolyte complexes are likewise suitable for preparing wound ointment preparations which contain, for example, antibiotics or proteins as regeneration promoters.

The polyelectrolyte complex microparticles according to the invention are also outstandingly suitable as air-containing echogenic contrast agents for ultrasonic diagnosis. Polyelectrolyte complex particles composed of hydrophobically esterified dextran sulfate and of a copolymer of PDAA and hydrophobically esterified PHEA (for abbreviations, see page 4) have proven particularly suitable for ultrasonic diagnosis.

The invention is explained in more detail hereinafter by means of examples. The particle size has been determined by microscopic methods or by filtration through filters of defined pore size and, in some cases, by Coulter counter (from Coulter Electronics) or flow cytometer.

EXAMPLES a) Preparation of polyelectrolyte complexes

Example 1

Complex of xylan polysulfate and poly-L-lysine 3800

A 0.1% aqueous solution of each of xylan polysulfate sodium salt (from BENE-Chemie) and of poly-L-lysine of average molecular weight 3800 (from Sigma) is made up. Sufficient HCl is added to the poly-L-lysine solution for the pH to be 3. The xylan polysulfate solution is likewise adjusted to pH 3 (HCl) and added dropwise via a metering pipette. The polyelectrolyte complex precipitates and is separated off by centrifugation and membrane filtration. After washing with $H_2O$, the microparticulate product can be freeze-dried. The particle size can be controlled by the vessel size, the stirring speed, the diameter of the dropwise addition nozzle and the dropping rate and can be adjusted from the region around 20 nm to 100 µm.

EXAMPLE 2

Complex of palmitoylxylan polysulfate with 20% palmitic acid residues and chitosan 0.1% solutions are prepared as in Example 1. The procedure corresponds to that employed in Example 1, only that no pH control is carried out in this case, and polylysine is replaced by chitosan (from Protan). The palmitoylxylan polysulfate can be prepared, for example, by the process described in German Patent Application P 3921761.2. Chitosan 143 is used. The resulting particles are large agglomerates (100 µm and larger) and can be reduced to a size of 1–4 µm by grinding in a mortar.

EXAMPLE 3

Polyelectrolyte complex particles composed of palmitoylxylan polysulfate with 20% palmitic acid and chitosan with incorporation of human serum albumin as model protein for vaccines.

The procedure is carried out as described in Example 2, only that 0.2% human serum albumin (from Sigma), dissolved in water, is added to the palmitoylxylan polysulfate solution before the dropwise addition. Particles in the range 2–5 µm can be obtained after grinding. See Example 10 for the determination of the albumin release.

EXAMPLE 4

Preparation of rabies vaccine/polyelectrolyte complex microparticles

Particles in the <5 µm range can be obtained with two different preparations:

I.

Polyacid: Palmitoylxylan polysulfate with 20% palmitic acid

Polybase: Lysine octadecyl ester

Auxiliary: ®Pluronic F68

50 mg of polyacid are dissolved in 5 ml of a 0.1% strength solution of rabies vaccine from Behringwerke (the solution is aqueous and contains 40% sucrose), the pH is 6.3. 50 mg of polybase are added to 5 ml of a 0.5% strength solution of ®Pluronic F68 in water. The polyacid/vaccine solution is added dropwise to the stirred polybase solution (which has pH 5.8). After centrifugation (10 min, 2000 rpm), the clear supernatant is separated off, and the residue is made into a paste with $H_2O$ and freeze-dried. Yield 779.7 mg of particles. The amount of the employed vaccine incorporated can be found by resuspension and analysis of the supernatant (in $H_2O$) to be 90%.

II.

Polyacid: Palmitoylxylan polysulfate with 20% palmitic acid

Polybase: 40:60 copolymer of poly-α,β-(2-dimethylaminoethyl)-D,L-aspartamide (40%) and poly-α,β-(2-palmitoyloxyethyl)-D,L-aspartamide (60%)

no auxiliary

Once again, two solutions are made up, each containing 50 mg of polyacid/base. The polyacid solution is identical to that in I. The polybase solution is identical to that in I except that it contains no ®Pluronic. Both solutions are adjusted to pH 7 and, as in I, centrifuged and the residue is made into a paste and freeze-dried. The incorporation efficiency corresponds to that in I. Yield: 76.5 mg.

EXAMPLE 5

Vaccination of mice against human serum albumin with polyelectrolyte complex microparticles The following microparticle preparations were employed:

Sample I: Xylan sulfate esterified with about 15% palmitic acid/lysine octadecyl ester +7% Pluronic®68, 5–30 µm Sample II: Xylan sulfate esterified with about 15% palmitic acid/lysine octadecyl ester, ≦10 µm Sample III: Xylan sulfate esterified with about 15% palmitic acid/poly-L-lysine 4 kDa +7% Pluronic® F68, 2–50 µm Sample IV: Polyaspartic acid 30 kDa/poly-α,β-(2-dimethylaminoethyl)-D,L-aspartamide/poly-α,β-(2-palmitoyloxyethyl)-D,L-aspartamide copolymer (40:60), <10 µm Sample V: Xylan sulfate/lysine octadecyl ester, 10–20 µm All the samples contained about 7% by weight human serum albumin (Behringwerke). These complexes were resuspended in concentrations of 66.67 µg/ml, 6.67 µg/ml and 0.67 µg/ml in PBS (phosphate-buffered saline). 0.3 ml of each vaccine was administered s.c. to, in each case, 10 NMRI mice weighing about 20 g. 14 weeks after the vaccination, the experimental animals were revaccinated with the same dose. The antibodies directed against human serum albumin in the serum of the experimental animals were quantified in an ELISA. Used as comparison was aluminum hydroxide $Al(OH)_3$ which is known as a good adjuvant and is contained in various vaccines.

ELISA titer after inoculation with 6.67 µg of formulation/ ml (average dose), 2, 4, 8, 14 (revaccination), 16 and 21 weeks after the first vaccination:

| Sample | Day 0 | Day 2 | Day 4 | Day 8 | Day 14 |
| --- | --- | --- | --- | --- | --- |
| I | <1:300 | <1:300 | 1:300 | 1:900 | 1:900 |
| II | <1:300 | <1:300 | 1:300 | <1:300 | <1:300 |
| III | <1:300 | 1:300 | 1:900 | 1:2700 | 1:8100 |
| IV | <1:300 | <1:300 | <1:300 | 1:2700 | 1:8100 |
| V | <1:300 | 1:900 | 1:2700 | 1:8100 | 1:24300 |
| Al(OH)$_3$ | <1:300 | 1:900 | 1:900 | 1:900 | 1:900 |

| Sample | Day 16 | Day 21 |
| --- | --- | --- |
| I | 1:72900 | 1:72900 |
| II | 1:24300 | 1:24300 |
| III | 1:72900 | 1:24300 |
| IV | 1:72900 | 1:72900 |
| V | 1:72900 | 1:72900 |
| Al(OH)$_3$ | 1:8100 | 1:24300 |

Administration of the same vaccine to guinea pigs likewise resulted in distinct seroconversion.

EXAMPLE 6

Polyelectrolyte complex particles composed of polyaspartic acid and poly-α,β-(2-dimethylaminoethyl)-D,L-aspartamide (PDAA) with incorporation of tetracycline as example of a low molecular weight active substance.

The procedure is as described in Example 3, except that a 0.2% solution of tetracycline in water is employed in place of human serum albumin. See Example 11 for the tetracycline release.

EXAMPLE 7

Polyelectrolyte complex particles composed of xylan polysulfate and daunoribicin.

10 mg of xylan polysulfate are dissolved in 0.5 ml of $H_2O$. 100 µl of a 10% daunorubicin solution (daunorubicin from Sigma) are diluted to 0.4 ml with water. The daunorubicin solution is added dropwise to the xylan polysulfate solution. The resulting suspension contains particles whose diameter is in the 5 µm range. See Example 12 for the daunorubicin release.

EXAMPLE 8

Polyelectrolyte complex particles composed of palmitoylxylan polysulfate with 20% palmitic acid, daunorubicin and lysine octadecyl ester.

1 ml of a solution which contains 1% each of daunorubicin and lysine octadecyl ester is adjusted to pH 4. A 1% solution of palmitoylxylan polysulfate, likewise 1 ml, likewise adjusted to pH 4, is added dropwise. The resulting suspension can no longer be fractionated by filtration. The particles can be adjusted by altering the concentration, the stirring speed, the dropping rate and the nozzle diameter in the range from 100 nm to 1 µm (see Table 1).

TABLE 1

| Particle size | Concentration | Stirring speed | Dropping rate | Nozzle diameter |
|---|---|---|---|---|
| 1 µm | 0.1% | 300 min$^{-1}$ | 100 min$^{-1}$ | 0.5 mm |
| 10 µm | 0.5% | 300 min$^{-1}$ | 100 min$^{-1}$ | 0.5 mm |
| 20 µm | 1% | 300 min$^{-1}$ | 100 min$^{-1}$ | 0.5 mm |
| 100 nm | 0.1% | 1000 min$^{-1}$ | 100 min$^{-1}$ | 0.5 mm |
| 20 nm | 0.1% | 1000 min$^{-1}$ | 100 min$^{-1}$ | 0.2 mm |
| 80 µm | 1% | 100 min$^{-1}$ | 100 min$^{-1}$ | 0.5 mm |
| 100 µm | 1% | 100 min$^{-1}$ | 200 min$^{-1}$ | 0.5 mm |

EXAMPLE 9

Echogenic injectable polyelectrolyte complex microparticles as ultrasonic contrast agent.

The polyelectrolyte complex particles are prepared as follows:

In each case a 1% strength aqueous solution at pH 7 is made up from dextran sulfate (M=6000) in which about 20% of the dextran OH groups have been esterified with caproic acid and the remaining OH groups have been sulfated ("hydrophobically esterified dextran sulfate", "polyacid ") and from a copolymer of poly-α,β-(2-dimethylaminoethyl)-D,n-aspartamide (60%) and poly-α,β-(2-palmitoyloxyethyl)-D,L-aspartamide (40%) ("polybase"). The polyacid solution is added dropwise to the polybase solution and stirred at room temperature for 10 minutes, the complex is removed by centrifugation, the solution is decanted off, and the solid is made into a paste with and freeze-dried.

Test as contrast agent:

Freeze-dried and resuspended microparticles with a size of the order of 1–3 µm are investigated in a phantom which represents a model of the heart and extremely small capillary vessels (lung model) for the ultrasonic contrast brought about by incorporated air. The particles pass through the capillaries unhindered.

b) Release tests

EXAMPLE 10

Release of albumin from the microparticles described in Example 3

A microparticle suspension in phosphate buffer is shaken continuously. After 1, 4, 7, 13, 21 add 28 days, the supernatant is removed and then the albumin content is determined by electrophoresis known from the literature. The result is a profile with 2 release maxima as is required for various vaccines:

| Release on day | 1 | 4 | 7 | 13 | 21 | 28 |
|---|---|---|---|---|---|---|
| Albumin released | 50 | 20 | <5 | <5 | 10 | <5 |

Particles are no longer present after somewhat more than one month.

EXAMPLE 11

Tetracycline release from the polyelectrolyte complex particles of Example 6.

The breakdown test is carried out as test 10. The active substance is determined by a UV spectroscopic method known from the literature.

The results are:

| Release on day | 1 | 4 | 7 | 13 |
|---|---|---|---|---|
| Tetracycline released | 30 | 10 | 10 | <5 |

EXAMPLE 12

Release of daunorubicin from the polyelectrolyte particles of Example 7.

The particle suspension is placed in a Soxhlet extractor and extracted with $H_2O$ for several days. Daunorubicin in the extract is determined by a fluorometric method known from the literature (at 472/555 nm). It emerges that the release, based on the total amount of daunorubicin weighed in, is as follows:

| after was: | 3.5 h 8.5% | 11 h 10.5% | 20 h 15.0% | 29 h 26.2% | the release of the amount |
|---|---|---|---|---|---| of active substance employed.

We claim:

1. A pharmaceutical composition consisting essentially of:
   a) a polyelectrolyte complex in microparticulate form,
   wherein said polyelectrolyte complex has an average particle size of less than 15 µm and is comprised of a polybase and a polyacid,
   wherein at least one of said polyacid and said polybase is a polymer, and
   wherein when said polyacid is a polymer, the polymer is selected from the group consisting of xylan polysulfates, dextran sulfates, poly(amino acids), polysaccharide polysulfates, inulin sulfates, hydroxyethylstarch sulfates, polysaccharide polysulfonates, polysaccharide polyphosphates, polyphosphates, and derivatives of said polymer, and wherein when said polybase is a polymer, the polymer is selected from the group consisting of poly-L-lysine, poly-α,β-(2-dimethylaminoethyl)-D,L-aspartamide, chitosan, lysine octadecyl ester, aminated dextrans, aminated cyclodextrins, aminated cellulose ethers, aminated pectins, and derivatives of said polymer; and b) a pharmaceutically effective amount of at least one active agent selected from the group consisting of an enzyme inhibitor, an antigen, a cytostatic, an antiinflammatory agent, an antibiotic, a vaccine and an ultrasonic contrast agent.

2. A pharmaceutical composition as claimed in claim 1, wherein at least one of said polyacid and said polybase contains said active agent.

3. A pharmaceutical composition as claimed in claim 1, wherein the microparticles further contain one or more auxiliaries.

4. A pharmaceutical composition as in claim 1, wherein the active agent is an ultrasonic contrast agent.

5. A pharmaceutical composition as claimed in claim 1, wherein the polyelectrolyte complex has an average particle size of $\leq 5$ μm.

6. The method of treating a patient in need of a vaccine which comprises administering a pharmaceutical composition as claimed in claim 1 as a vaccine.

7. The method of diagnosing a patient using a diagnostic aid comprising a pharmaceutical composition as claimed in claim 1.

8. The method of treating a patient comprising administrations of a pharmaceutical composition as claimed in claim 1 as a therapeutic agent.

9. The method of treating a patient in need of diagnosis with an ultrasonic diagnostic aid comprising administration of a pharmaceutical composition as claimed in claim 1.

10. The method of treating a patient comprising parenteral administration of a pharmaceutical composition as claimed in claim 6.

11. A pharmaceutical composition as claimed in claim 1, wherein the active agent is an active peptide.

12. A pharmaceutical composition as claimed in claim 1, wherein the active agent is a protein.

13. A pharmaceutical composition as claimed in claim 1, wherein the active agent is an enzyme.

* * * * *

UNITED STATES PATENT AND TRADEMARK OFFICE
CERTIFICATE OF CORRECTION

PATENT NO.   : 5,700,459
DATED        : December 23, 1997
INVENTOR(S)  : Volker KRONE et al.

It is certified that error appears in the above-indentified patent and that said Letters Patent is hereby corrected as shown below:

Claim 4, column 9, line 18, after "composition as", insert --claimed--.

Claim 8, column 10, lines 7-8, "administrations" should read --administration--.

Signed and Sealed this

Twenty-first Day of April, 1998

Attest:

BRUCE LEHMAN

Attesting Officer        Commissioner of Patents and Trademarks